United States Patent [19]

Mita et al.

[11] Patent Number: 4,962,222

[45] Date of Patent: Oct. 9, 1990

[54] PREPARATION PROCESS OF α-L-ASPARTYL-L-PHENYLALANINE METHYL ESTER HAVING LOW HYGROSCOPICITY

[75] Inventors: Ryuichi Mita; Toshio Katoh, both of Kawasaki; Chojiro Higuchi, Kamakura; Takeshi Oura, Zushi; Akihiro Yamaguchi, Kamakura, all of Japan

[73] Assignee: Mitsui Toatsu Chemicals, Incorporated, Tokyo, Japan

[21] Appl. No.: 300,724

[22] Filed: Jan. 25, 1989

Related U.S. Application Data

[63] Continuation of Ser. No. 130,172, Dec. 8, 1987, abandoned.

[30] Foreign Application Priority Data

Dec. 19, 1986 [JP] Japan ................. 61-301469

[51] Int. Cl.$^5$ ............................................. C07C 101/02
[52] U.S. Cl. .................................................... 560/41
[58] Field of Search ........................................ 560/41

[56] References Cited

U.S. PATENT DOCUMENTS

| | | | |
|---|---|---|---|
| 3,879,372 | 4/1975 | Boesten | 260/112.5 |
| 3,933,781 | 1/1976 | Bachman et al. | 260/112.5 |
| 4,021,418 | 5/1977 | Takemoto et al. | 260/112.5 |
| 4,071,511 | 1/1978 | Takemoto et al. | 260/112.5 |
| 4,088,649 | 5/1978 | Smith et al. | 544/385 |
| 4,153,737 | 5/1979 | Berg et al. | 426/548 |
| 4,579,747 | 4/1986 | Sugiyama et al. | 426/548 |
| 4,634,790 | 1/1987 | Shinohara et al. | 560/40 |
| 4,835,301 | 5/1989 | Wakamatsu et al. | 560/41 |

FOREIGN PATENT DOCUMENTS

| | | |
|---|---|---|
| 0092933 | 11/1983 | European Pat. Off. |
| 0127411 | 12/1984 | European Pat. Off. |
| 2559773 | 4/1985 | France |
| 46-1370 | 2/1971 | Japan |
| 48-96557 | 12/1973 | Japan |
| 51-40069 | 1/1976 | Japan |
| 51-113841 | 7/1976 | Japan |
| 53-82752 | 7/1978 | Japan |
| 59-130846 | 7/1984 | Japan |
| 59-219258 | 12/1984 | Japan |
| 59-225152 | 12/1984 | Japan |
| 59-225153 | 12/1984 | Japan |
| 60-50200 | 3/1985 | Japan |
| 60-174799 | 9/1985 | Japan |
| 1359123 | 7/1974 | United Kingdom |
| 1464140 | 2/1977 | United Kingdom |
| 2133409 | 7/1984 | United Kingdom |

OTHER PUBLICATIONS

Chemical Abstracts, 105:153551s (1986).
English–Language abstract (World Patent Index) of JP 58-185545.

*Primary Examiner*—Bruce Gray
*Attorney, Agent, or Firm*—Fisher, Christen & Sabol

[57] ABSTRACT

α-L-Aspartyl-L-phenylalanine methyl ester having low hygroscopicity is prepared by bringing a cake of α-L-aspartyl-L-phenylalanine methyl ester, which cake has been obtained by solid-liquid separation through a desired preparation process of α-L-aspartyl-L-phenylalanine methyl ester, into contact with an organic solvent of uniform phase so as to treat the cake with the organic solvent, subjecting the resulting mixture of the cake and organic solvent to solid-liquid separation to obtain a cake, and then drying the last-mentioned cake at a temperature not higher than 60° C. The organic solvent is dry or contains water in an amount up to 30 wt.%.

8 Claims, No Drawings

PREPARATION PROCESS OF α-L-ASPARTYL-L-PHENYLALANINE METHYL ESTER HAVING LOW HYGROSCOPICITY

This application is a continuation of prior U.S. patent application Ser. No. 130,172, filing date 12/07/87 now abandoned.

BACKGROUND OF THE INVENTION

1. Field of the Invention

This invention relates to a process for the preparation of α-aspartyl-L-phenylalanine methyl ester having low hygroscopicity and excellent storage stability.

2. Related Art

α-L-aspartyl-L-phenylalanine methyl ester (hereinafter abbreviated as "α-APM") is a substance useful as a sweetening agent. It is nearly 200 times as sweet as sucrose and moreover, its sweet taste resembles that of sugar. For these reasons, its demand is growing these days as a dietary sweetening agent.

α-APM is known to have either one of two crystalline forms having different hygroscopicity, namely, form I and form II. The crystalline form I has high hygroscopicity so that the water content at equilibrium may reach as high as 10 percent. In contrast, the crystalline form II has low hygroscopicity and the water content is as low as about 3 percent at equilibrium (U.S. Pat. No. 4,579,747).

When α-APM of the crystalline form I is provided as a final product, its water content increases due to its high hygroscopicity after its production until its shipping so that it tends to become an off-specification product (the water content of α-APM is specified to be 4.5% max. in the Japanese Standard for Food Additives). It is hence necessary to pay special attention to the storage of products. Even when formed together with one of various vehicles into a sweetener in the form of either granules or tablets, the sweetener may undergo browning In the case of granules, it is known that the flowability of the granules tends to drop on storage In the case of tablets on the other hand, the readiness of their disintegration upon addition to water is known to have tendency to deteriorate in the course of their storage The thus-reduced flowability and disintegration readiness are known to lead to a reduction in solubility.

When α-APM is provided as a final product of the crystalline form II on the other hand, such troubles seldom occur. It is hence desired to prepare α-APM in the crystalline form II and to formulate it into a final product in the same crystalline form.

As processes for the preparation of α-APM, a variety of processes have already been disclosed, centering on chemical processes. Various preparation processes have been known including, for example, to subject an N-protected-L-aspartic anhydride and L-phenylalanine methyl ester to condensation and then to deprotect the resultant N-protected-α-L-aspartyl-L-phenylalanine methyl ester or to esterify N-formyl-α-L-aspartyl-L-phenylalanine, which has been obtained by condensing N-formyl-L-aspartic anhydride and L-phenylalanine, or its deformylation product, i.e., α-L-aspartyl-L-phenylalanine in a medium composed of hydrochloric acid and methanol Whichever process is employed, α-APM is processed and/or treated into a final product by conducting its purification such as recrystallization. It is however usual to subject α-APM to purification such as recrystallization from water or a mixed solvent of an alcohol and water and then to dry the thus-purified crystals into a final product, since α-APM is either insoluble or hardly soluble in organic solvents However, α-APM crystals obtained by such purification generally have the crystalline form I and are hence high in hygroscopicity and poor in storage stability.

Regarding the preparation of II-form crystals having low hygroscopicity, only one process has been known in which form-I crystals obtained by a conventional process are dried at a temperature of 80° C or higher so as to convert their crystalline form from I to II (U.S. Pat. No. 4,579,747).

α-APM is however susceptible to an intramolecular cyclizing reaction as readily envisaged from its structure, so that it tends to be converted into a diketopiperazine compound (5-benzyl-3,6-dioxopiperazine-2-acetic acid) having no sweet taste Accordingly, the product specification rules the tolerable maximum content of the above compound (The tolerable content of the above compound in α-APM is specified to be 1.5 percent max. according to the Japanese Standard for Food Additives). Since α-APM is dried at an elevated temperature of 80° C. or higher in the known process described above, the byproduction of an undesirable compound, i.e., the above-described diketopiperazine compound tends to occur. As a result, reprocessing may be indispensable in some instances so as to lower the content of the above compound below the value specified for the product.

Incidentally, the present inventors reproduced Preparation Example 1 described in the U.S. patent specification referred to above, namely, dried at 90° C. and under reduced pressure crystals of α-APM which had been obtained by conducting filtration and water-washing subsequent to the neutralization of α-APM hydrochloride with a 10 percent aqueous solution of sodium carbonate in water. As a result, the thus-obtained α-APM was certainly found to have the crystalline form II from its X-ray diffraction spectrum Upon analysis of the content of the diketopiperazine compound, α-APM was however found to contain it in an amount as much as 2.3 percent. This data is apparently higher than the tolerable maximum level specified for the diketopiperazine compound As demonstrated by the above experiment of the present inventors, the process in which α-APM is dried under temperature conditions of 80° C. or higher tends to induce byproduction of one or more undesirable compounds and is thus not considered to be a preferable process from the industrial viewpoint.

It is essential to reduce the drying temperature substantially in order to minimize or inhibit the byproduction of the diketopiperazine compound It has accordingly been desired to develop a process which can provide II-form crystals by drying α-APM at a relatively low temperature.

SUMMARY OF THE INVENTION

An object of this invention is to provide an improved process for preparing II-form α-APM crystals having low hygroscopicity .

Another object of this invention is to provide a process which can prepare II-form α-APM crystals of low hygroscopicity even when drying is effected under milder temperature conditions in order to inhibit the byprodution of the diketopiperazine compound upon drying.

The present inventors have carried out an extensive investigation in order to achieve the above objects. As a result, it has been found surprisingly that II-form crystals having sufficiently low hygroscopicity can be still prepared even when dried under milder conditions of 60° C. or lower, i.e., without need for drying at a temperature as high as 80° C. or even higher so long as a wet cake of α-APM obtained through a desired preparation process is washed, for example, with methanol By way of example, a wet cake of α-APM was obtained by subjecting α-APM hydrochloride to isoelectric neutralization with an aqueous solution of sodium carbonate in water to crystallize out α-APM and then subjecting the resultant mixture to solid-liquid separation A portion of the wet cake was washed four times with methanol of a weight as much as 1 times the α-APM in the portion of wet cake to obtain another wet cake. A portion of the first-mentioned wet cake and said another wet cake were dried respectively at 40°–45° C. under reduced pressure. With respect to dry products thus obtained, their losses in weight upon drying were determined respectively by the method prescribed in the Japanese Standard for Food Additives (105° C./4 hours). The water contents of the former and latter dry products were found to be 5.3 percent and 1.9 percent respectively As a result of X-ray diffraction spectrum measurements, the former and latter dry products were found to be I-form crystals and II-form crystals respectively As a result of a further detailed investigation on the above process, it has also been found that the washing methanol is not absolutely required to be dry and may contain water in an amount up to about 30 wt. percent, the wet cake may be stirred in a solvent instead of its washing, and the solvent is not limited to methanol and other dry or water-containing polar solvents capable of forming a uniform phase with water may also be used. The process of this invention has hence been reached In one aspect of this invention, there is thus provided a process for the preparation of α-L-aspartyl-L-phenylalanine methyl ester (II-form α-APM crystals) having low hygroscopicity, which comprises the following consecutive steps:

(i) bringing a cake of α-L-aspartyl-L-phenylalanine methyl ester, which cake has been obtained by solid-liquid separation through a desired preparation process of α-L-aspartyl-L-phenylalanine methyl ester, into contact with an organic solvent of uniform phase which is dry or contains water in an amount up to 30 wt. percent, thereby treating the cake with the organic solvent;

(ii) subjecting the resulting mixture of the cake and organic solvent to solid-liquid separation so to obtain a cake; and (iii) drying the last-mentioned cake at a temperature not higher than 60° C.

The process of this invention is effective not only as a preparation process of α-APM having low hygroscopicity but also as a process for the removal of the above-mentioned diketopiperazine compound where the diketopiperazine compound is byproduced in the preparation process of α-APM, for example, in its purification step or the like and still remains in a wet cake of α-APM purified and isolated finally.

According to the process of this invention, α-APM crystals having low hygroscopicity can be obtained by a simple operation of washing or stirring in an organic solvent or a water-containing organic solvent of uniform phase, followed by drying under mild conditions, i.e., at temperatures not exceeding 60° C. Use of such lower drying temperatures has made it possible to reduce or inhibit the byproduction of impurities such as the diketopiperazine compound upon drying, whereby the preparation of α-APM of stable quality has been materialized The present invention has great significance from the industrial standpoint.

DETAILED DESCRIPTION OF THE INVENTION

Regarding α-APM cakes to which the process of the present invention is applied, no particular limitation is imposed on their preparation process. The process of this invention may be applied to α-APM cakes obtained by various processes. Namely, the process of this invention can be applied to a cake obtained by the solid-liquid separation of α-APM crystals from their corresponding mother liquor. The α-APM crystals may be obtained in various ways, for example, by esterifying α-L-aspartyl-L-phenylalanine in a medium of hydrochloric acid and methanol and then neutralizing the resulting α-APM hydrochloride with a base in water, by recrystallizing and purifying the above-obtained α-APM crystals from water or a mixed solvent of water and an alcohol, or by catalytically reducing N-benzyloxycarbonyl-a-L-aspartyl-L-phenylalanine methyl ester in a medium of an alcohol and water and after separation of a catalyst, crystallizing the reaction product.

In the process of this invention, an α-APM cake obtained by solid-liquid separation through the desired preparation process of α-L-aspartyl-L-phenylalanine methyl ester is brought into contact with an organic solvent of uniform phase which may be dry or may contain water in an amount up to 30 wt. percent, whereby the cake is treated with the organic solvent. For example, the cake is washed with an organic solvent of uniform phase which may be dry or may contain water in an amount up to 30 wt. percent, or is stirred an organic solvent of uniform phase which may be dry or may contain water in an amount up to 30 wt. percent. The resulting mixture is subjected to solid-liquid separation and an α-APM cake thus obtained is thereafter dried at temperatures not higher than 60° C.

No particular limitation is imposed on the manner of the contact between the α-APM cake and the organic solvent for the treatment of the α-APM cake with the organic solvent, so long as α-APM is allowed to contact sufficiently with the organic solvent. As specific modes for carrying out the above contact and treatment, the following two methods may be mentioned by way of example.

In a first method, a wet cake of α-APM obtained by one of various preparation processes is washed with an organic solvent of uniform phase which may be dry or may contain water in an amount up to 30 wt. percent. Since an α-APM cake obtained by solid-liquid separation remains in a separator (filter), it is only necessary to pour a desired organic solvent, which may optionally contain water in an amount up to about 30 wt. percent into the α-APM cake so as to wash the α-APM cake.

In a second method, a wet cake of α-APM prepared by one of various preparation processes and obtained eventually by solid-liquid separation is thrown into an organic solvent of uniform phase. After stirring, the resulting mixture is subjected again to solid-liquid separation. In this case, the organic solvent to be used in the second method is not necessarily required to be dry. Including the water contained in a wet α-APM cake, the organic solvent phase in the stirring treatment is a uniform system and may contain water in an amount up to 30 wt. percent.

No particular limitation is imposed on the organic solvent to be used in these methods, so long as it can form a uniform system with water. Taking the subsequent drying into consideration, a solvent whose boiling point is up to about 120° C. under normal pressure is selected.

Specific examples of the organic solvent may include alcohol type solvents such as methanol, ethanol, 1-propanol, 2-propanol, 1-butanol, 2-butanol, isobutanol and tert-butanol; ketone type solvents such as acetone and methyl ethyl ketone; carboxylic acid type solvents such as formic acid and acetic acid; ester type solvents such as methyl formate, ethyl formate and methyl acetate; ether type solvents such as dioxane and tetrahydrofuran; 2-methoxyethanol; acetonitrile; etc. Among these, alcohol type solvents, ketone type solvents, ether type solvents and acetonitrile are used primarily. It is unnecessary for these solvents to be dry substantially. It is hence possible to use an organic solvent of uniform phase which contain water in a certain amount. The permissible water content is 30 wt. percent or less, preferably, 20 wt. percent or less in the first method, while the permissible water content at the time of the stirring treatment is 30 wt. percent or less, preferably, 20 wt. percent or less, including the water content of the $\alpha$-APM cake, in the second method. A practically dry organic solvent may also be used obviously. If the water content exceeds the upper limit, the objects of this invention cannot be achieved irrespective of the amount of a solvent used even when the resulting $\alpha$-APM cake is dried under mild conditions not exceeding 60° C. Among the organic solvents exemplified above, there are some organic solvents whose maximum water contents permitting the formation of a uniform organic solvent phase are less than 30 wt. percent, although the maximum water contents vary depending on temperature. When such a solvent is used, use of an organic solvent containing water in a amount smaller than the maximum water content capable of forming a uniform system is essential for achieving the objects of this invention.

If the organic solvent is used too little, the subsequent mild drying alone is not sufficient to attain the objects of this invention. On the other hand, it is not economical to use the organic solvent in any unduly large amount in view of the recovery of the solvent. In the first method, i.e., the washing method, the organic solvent may be used in an amount 1-10 times as heavy as an $\alpha$-APM cake. In the second method, the organic solvent may be used in an amount sufficient for the stirring treatment of an $\alpha$-APM cake, generally, as heavy as 2-20 times the $\alpha$-APM cake.

Whichever method is chosen, it is unnecessary to conduct the contact and treatment at any particularly high temperature.

In various preparation processes, an $\alpha$-APM cake eventually begins to separate out at the surrounding environmental temperature or a temperature lower than that in general. Therefore, the contact and treatment is effected generally at the surrounding environmental temperature or at a temperature lower than that, specifically, at 0°-40° C. No problems arise even when the contact and treatment is conducted at temperatures outside the above range. Use of such temperatures however disadvantageous from the viewpoints of the recovery rate of $\alpha$-APM and the efficiency of energy.

An $\alpha$-APM cake obtained in the above manner is then dried. It is unnecessary to conduct this drying at any particularly high temperatures. Mere drying under mild temperature conditions of 60° C. or lower is sufficient to obtain $\alpha$-APM crystals having low hygroscopicity.

The drying may be carried out under normal pressure, reduced pressure or aerated conditions.

By way of summary, the present invention involves a process for the preparation of $\alpha$-L-aspartyl-L-phenylalanine having low hygroscopicity, which comprises bringing a cake of $\alpha$-L-aspartyl-L-phenylalanine methyl ester, which cake has been obtained by solid-liquid separation through a desired preparation process of $\alpha$-L-aspartyl-L-phenylalanine methyl ester, into contact with an organic solvent of uniform phase so as to treat the cake with the organic solvent, subjecting the resulting mixture of the cake and organic solvent to solid-liquid separation to obtain a cake, and then drying the last-mentioned cake at a temperature not higher than 60° C. The organic solvent is dry or contains water in an amount up to 30 weight percent.

The present invention will hereinafter be described in detail by the following Examples.

EXAMPLE 1:

In 300 ml of water, 36.7 g (0.1 mole) of $\alpha$-APM.HCl dihydrate was suspended. While stirring at room temperature, a 10percent aqueous solution of sodium carbonate was gradually added dropwise until the pH reached 5.2. After stirring the reaction mixture for 1 hour at room temperature, it was cooled to 5° C. Crystals of $\alpha$-APM precipitated were collected by filtration and then washed with chilled water. Thereafter, the resultant wet cake was washed 4 times with 20 ml portions of methanol. The thus-obtained cake was divided into equal half portions. One of the portions was dried at 40-45° C. under reduced pressure while the other portion was dried at 40-45° C. under normal pressure. After the drying, their weights were 12.9 g and 13.1 g respectively.

From the thus-obtained dry products, 1.0 g samples were weighed precisely and their losses in weight on drying were measured at 105° C. for 4 hours under normal pressure. Their losses in weight on drying were 1.8percent and 2.0percent, respectively. Their respective X-ray diffraction spectra indicated II-form crystals. The thus-obtained crystalline samples were both left over at 30° C. and 80% R.H. Sampling was conducted periodically so as to investigate their weight losses along the passage of time at 105° C. for 4 hours, whereby their hygroscopicity was studied. In each of the samples, the loss in weight on drying did not exceed 3.2% and the weight became constant when the loss in weight on drying was in a range of 3.0-3.2%. L Examples 2-8 Comparative Example 1:

In the same manner as in Example 1, 36.7 g (0.1 mole) of $\alpha$-APM.HCl dihydrate was neutralized with a 10% aqueous solution of sodium carbonate in water, followed by filtration and chilled water washing to obtain $\alpha$-APM crystals. Those crystals were recrystallized and purified from 250 ml of 50% (vol. %) methanol. After cooling to 5° C., a cake was obtained by filtration. Portions of the cake were washed separately while changing the kind and water content of the solvent. Cakes thus obtained were dried separately at 40-45° C. under reduced pressure. With respect to each dry product, were determined the loss in weight on drying (105° C./4 hours), and in terms of loss in weight on drying, the degree of hygroscopicity after left over for 2 days at 30° C. and 80% R.H. Results are shown in Table 1.

TABLE 1

| Ex. No. | Washing solvent | | α-APM | | |
|---|---|---|---|---|---|
| | Kind | Amount (ml) | Yield (g) | Loss in weight* on drying (%) | Hygroscopicity** (%) |
| 2 | Methanol | 20 × 4 times | 24.3 | 1.9 | 2.8 |
| 3 | 80% (w/w)methanol | " | 24.8 | 2.3 | 3.1 |
| 4 | 90% (w/w)methanol | " | 25.2 | 2.1 | 2.9 |
| 5 | Isopropanol | " | 24.4 | 1.8 | 3.0 |
| 6 | Dioxane | " | 23.9 | 2.6 | 3.6 |
| 7 | Acetonitrile | " | 24.1 | 2.9 | 3.8 |
| 8 | Acetone | " | 24.6 | 2.1 | 2.9 |
| Comp. Ex. | 60% (w/w)methanol | " | 25.4 | 4.6 | 9.4 |

*Loss in weight after heat-treated at 105° C. for 4 hours.
**Loss in weight on drying was measured after allowing each sample to stand for 2 days at 30° C. and 80% R.H and then heat-treating the sample at 150° C. for 4 hours. The hygroscopicity is indicated in terms of loss in weight.

Example 9:

In the same manner as in Example 1, 36.7 g (0.1 mole) of α-APM.HCl dihydrate was neutralized with a 10% aqueous solution of sodium hydroxide in water, followed by filtration and chilled water washing to obtain α-APM crystals. Amount of a wet cake: 59.8 g (α-APM content: 26.1 g). The wet cake was treated under stirring for 1 hour at room temperature in 330 ml of methanol, followed by filtration. Crystals thus obtained were dried at 50–60° C. under reduced pressure to obtain 24.0 g of α-APM. Its loss in weight on drying was measured in the same manner as in Example 1. As a result, the the loss in weight on drying was found to be 2.0%. A sample which had been left over for 2 days at 30° C. and 80% R.H. had a weight loss of 3.1% on drying.

COMPARATIVE EXAMPLE 2:

The wet cake of α-APM obtained by neutralizing α-APM.HCl in Example 9 was treated under stirring at room temperature for 1 hour in 330 ml of water which contained 65 wt. % of methanol, followed by filtration. After drying the resultant crystals at 50–60° C. under reduced pressure, 23.8 g of α-APM was obtained. Its loss in weight on drying and that of a sample of the crystals after allowing it to stand at 30° C. and 80% R.H. for 2 days were 4.8% and 9.3% respectively.

EXAMPLE 10:

Following the procedure of Example 1, 36.7 g (0.1 mole) of α-APM.HCl dihydrate was neutralized with a 10% aqueous solution of sodium carbonate in water, followed by collection of the thus-precipitated crystals by filtration and their washing with chilled water to obtain a wet cake of α-APM.

The resultant wet cake was recrystallized and purified from a mixed solvent composed of 150 ml of methanol and 150 ml of water. A wet α-APM cake thus crystallized and separated was washed four times with 30-ml portions of methanol. The resultant cake was dried at 40–45° C. under reduced pressure, thereby obtaining 23.8 g of α-APM in a purified form.

As a result of a measurement of its loss in weight on drying, its loss in weight on drying was found to be 1.7%. An X-ray diffraction spectrum indicated II-form crystals. A sample of the aboveobtained α-APM was left over for 2 days at 30° C. and 80% R.H. The weight loss of the sample on drying was 2.9%.

We claim:

1. A process for the preparation of type II α-L-aspartyl-L-phenylalanine methyl ester crystals having low hygroscopicity, which comprises the following consecutive steps:
   (i) bringing a first cake of α-L-aspartyl-L-phenylalanine methyl ester, the first cake having been obtained by solid-liquid separation through a desired preparation process of α-L-aspartyl-L-phenylalanine methyl ester, into contact with an organic solvent of uniform phase which is dry or contains water in an amount up to 30 weight percent, thereby treating the first cake with the organic solvent;
   (ii) subjecting the resultant mixture of the first cake and organic solvent to solid-liquid separation to obtain a second cake; and
   (iii) drying the second cake at a temperature not higher than 60° C.

2. The process as claimed in claim 1, wherein the contact between the first-mentioned cake and the organic solvent for the treatment of the former with the latter is effected by washing the first-mentioned cake with the organic solvent.

3. The process as claimed in claim 1, wherein the contact between the first-mentioned cake and the organic solvent for the treatment of the former with the latter is effected by stirring the first-mentioned cake in the organic solvent.

4. The process as claimed in claim 1, wherein the organic solvent is an alcohol solvent.

5. The process as claimed in claim 4 wherein the alcohol solvent is selected from the group consisting of methanol, ethanol, 1-propanol, 2-propanol, 1butanol, 2-butanol, isobutanol and tert-butanol.

6. The process as claimed in claim 1 wherein the organic solvent is an alcohol, a ketone, a carboxylic acid or an ether.

7. The process as claimed in claim 1 wherein the organic solvent is a ketone, a carboxylic acid, an ether or acetonitrile.

8. A process for the preparation of Type II α-L-aspartyl-L-phenylalanine methyl ester crystals having low hygroscopicity, which comprises the following consecutive steps:
   (i) bringing a first cake of α-L-aspartyl-L-phenylalanine methyl ester, the first cake having been obtained by solid-liquid separation through a desired preparation process of α-L-aspartyl-L-phenylalanine methyl ester, into contact with an organic solvent of uniform phase which is dry or contains water in an amount up to 30 weight percent, thereby treating the first cake with the organic solvent, the organic solvent being selected from the group consisting of acetone, methyl ethyl ketone, formic acid, acetic acid, methyl formate, ethyl formate, methyl acetate, acetone, dioxane, tetrahydofuran, 2-methaxyethanol and acetonitrile;

(ii) subjecting the resultant mixture of the first cake and organic solvent to solid-liquid separation to obtain a second cake; and (iii) drying the second cake at a temperature not higher than 60° C.

* * * * *